United States Patent [19]
Reichler et al.

[11] 4,121,466
[45] Oct. 24, 1978

[54] LIQUID DISPENSER WITH AN IMPROVED PROBE

[75] Inventors: Allen Reichler, Pearl River, N.Y.; Herman Guy Diebler, North Haledon, N.J.

[73] Assignee: Technicon Instruments Corporation, Tarrytown, N.Y.

[21] Appl. No.: 788,943

[22] Filed: Apr. 19, 1977

[51] Int. Cl.² ............................................. G01N 1/14
[52] U.S. Cl. ............................................. 73/423 A
[58] Field of Search ............... 23/230 R; 222/420; 73/423 A

[56] References Cited
U.S. PATENT DOCUMENTS
3,479,141  11/1969  Smythe et al. ............... 73/423 A Primary Examiner—Stanley H. Tollberg
Attorney, Agent, or Firm—S. P. Tedesco; Robert S. Salzman

[57] ABSTRACT

A metering apparatus is adaptable either as a dispenser or a sampler, the surface of the aspirating probe being coated with a thin film of liquid immiscible with the liquids to be aspirated. The thin immiscible film prevents contamination between segments of successively aspirated liquids and, also, their respective sources. Further, segments of the immiscible liquid can be aspirated between successive liquid segments, to maintain such liquid segments discrete.

19 Claims, 6 Drawing Figures

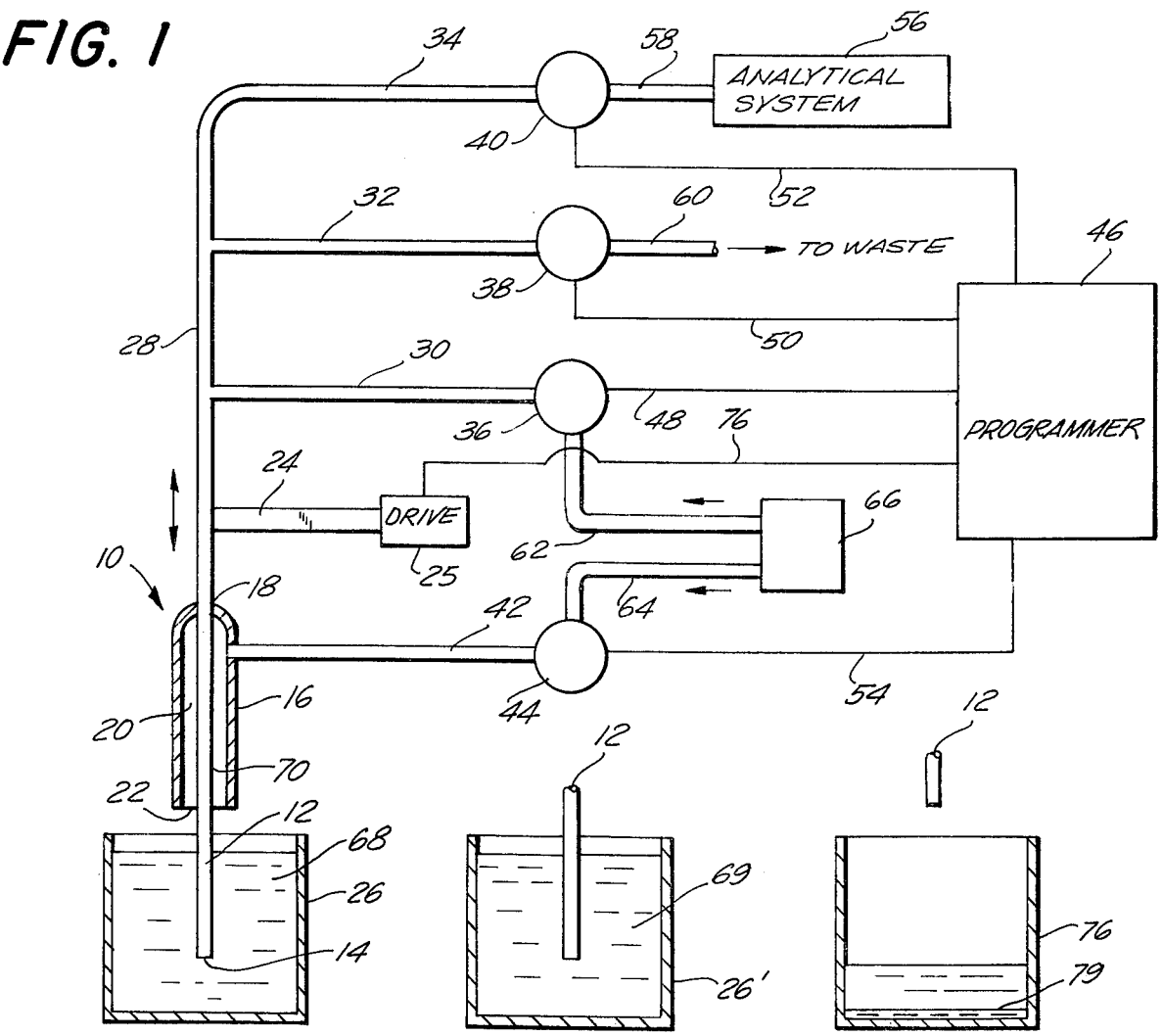
FIG. 1
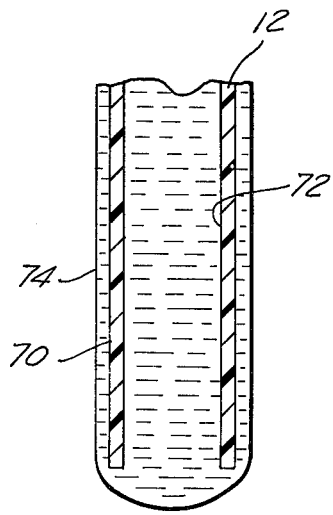
FIG. 2
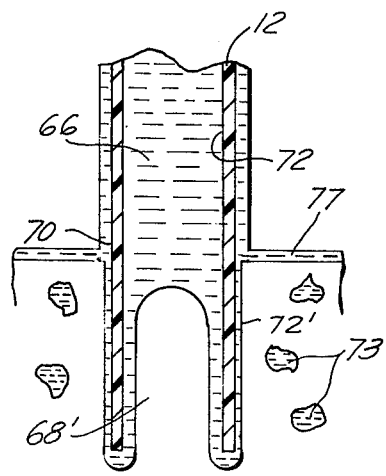
FIG. 3
FIG. 4  FIG. 5  FIG. 6

LIQUID DISPENSER WITH AN IMPROVED PROBE

BACKGROUND OF THE INVENTION

1. Field of the Invention

This invention relates to metering apparatus for aspirating discrete liquid volumes, either for subsequent dispensing or passing to an analytical system, wherein contamination between successively aspirated volumes is avoided.

2. Description of the Prior Art

In prior art metering apparatus, contamination between successively aspirated liquid volumes has been a major problem. Such contamination can result, for example, from residue remaining on the probe surfaces from a previously aspirated liquid volume. The avoidance of contamination is of particular concern where segments of sample liquids are successively aspirated, in precise volumes, for the analysis of different constituents of interest, for example, as in continuous-flow analytical systems of the type described in the Skeggs et al U.S. Pat. No. 3,241,432, issued on Mar. 22, 1966 and in the Smythe et al U.S. Pat. No. 3,479,141, issued on Nov. 18, 1969. In such systems, contamination has been significantly reduced by aspirating a segment wash liquid between successive sample segments, adjacent sample segments being separated by a sequence of air-wash liquid-air segments. To this end, the aspirating probe is immersed into a wash liquid reservoir between successive sample immersions, which serves to remove contaminants from both the interior and peripheral probe surfaces. Also, U.S. Pat. No. 3,479,141 teaches that contamination between successive sample liquids in continuous-flow analytical systems is very significantly reduced by introducing a liquid segment, e.g., silicone, which is immiscible with the aqueous sample segments and preferentially wets the interior surfaces of the probe and conduit system. In such event, the successive sample segments are, in effect, encased within the immiscible fluid, and not in contact with the interior conduit surfaces.

Also, in the case of metering apparatus of the dispenser-type, the aspirating probe is immersed into successive liquids, either samples or reagents, which are aspirated and dispensed, sequentially and in precise volumes. Such dispensing is effected by the use of a pilot fluid, which serves to "back-flush" contaminants from the interior surface of the probe system. Again, possible contamination resulting from residues on the peripheral probe surfaces has been avoided by immersing the probe into a wash liquid reservoir, and aspirating and dispensing such liquid to remove contaminants from both the interior and peripheral probe surfaces.

The removal of contaminants from the peripheral probe surfaces has required that the probe movement be other than rectilinearly, that is, to transport the probe from an aspirating station to a wash station. Also, it is necessary that the probe surfaces, both interior and peripheral, be washed between successive aspirations. This need to actively wash the probe surfaces necessarily reduces the rate at which precise liquid volumes can be aspirated or dispensed, and, also, requires a more complicated probe-driving mechanism.

OBJECTS OF THE INVENTION

Accordingly, an object of this invention is to provide an improved metering system, wherein the problem of contamination between successively aspirated samples is substantially avoided.

Another object of this invention is to provide an improved metering system, wherein the allowable aspirating rate is increased by avoiding the need to actively wash the probe system between successive liquid aspirations.

A further object of this invention is to provide an improved metering system, wherein a plurality of sample liquids can be aspirated successively into the probe system, without contamination between the aspirated sample liquids within the probe system or of the respective sources from which they have been aspirated.

Another object of this invention is to provide an improved metering system, wherein the probe system is inherently non-contaminating of the respective sources of liquids into which it is successively immersed.

These and other objects and features of the present invention are achieved by providing over the peripheral and internal surfaces of the probe proper a thin film of liquid which is characterized as being immiscible with the sample liquids to be aspirated and, also, which preferentially wets the internal and peripheral probe surfaces to the exclusion of such sample liquids. Such thin film can be defined, for example, by flowing the immiscible liquid over the peripheral surfaces and aspirating the run-off along the probe or immersing the probe into a reservoir of such liquid. The immiscible liquid may have a specific density which is greater or less than that of the liquids to be aspirated. For example, in the preferred embodiment, the immiscible liquid is flowed continuously down the peripheral probe surface at a rate substantially equal to the aspiration rate of the probe system, such as to be eventually aspirated on probe inlet. If desired, the flow of such immiscible liquid can be discontinued upon immersion of the probe inlet into a receptacle containing liquid to be aspirated. During immersion, excess immiscible liquid on the peripheral probe surface is floated onto the surface of the liquid being aspirated, but a small film remains on such surface portion. Also, during aspiration of the liquid, a thin film of the immiscible liquid continuously wets the interior probe surface. Accordingly, both peripheral and interior probe surfaces are constantly wetted and, hence, continuously protected by a thin film of the immiscible liquid. As the probe is withdrawn, the flow of immiscible liquid may be commenced, so to be aspirated along the probe immediately upon withdrawal of such probe from the liquid being aspirated. In such event, segments of the immiscible liquid and aspirated liquid segments are successively passed along the probe system, in turn, without the peripheral and internal surfaces of the probe being contacted by the aspirated liquid. The aspirated liquid segment can be dispensed or, alternatively, a next receptacle containing a different liquid can be positioned under the probe, in conventional fashion, whereby such liquid is aspirated upon immersion of the probe therein, for passage along the probe system.

Significantly, as an immiscible liquid segment is aspirated immediately prior and subsequent to each liquid segment passed into the probe system and preferentially wets both the interior and peripheral surfaces, the successively aspirated liquid segments are maintained discrete while passing along the probe system, e.g., to a continuous-flow analytical system, as shown. Accordingly, there is no contamination between the aspirated liquid segments passed along the probe system and, also, between their respective sources upon immersion of the probe therein, due to the presence of a thin protective film of immiscible liquid over the probe surfaces. Such result is achieved without the need of active washing of the interior and peripheral probe surfaces.

BRIEF DESCRIPTION OF THE DRAWINGS

FIG. 1 is a schematic view of a metering system according to the present invention, which is adaptable either as a dispenser or sampler.

FIGS. 2 and 3 further illustrate the operation of the dispenser during the aspiration and discharge cycles.

FIGS. 4, 5, and 6 are fragmentary views illustrating the liquid segments within the probe system, during different operating cycles of the metering system.

DETAILED DESCRIPTION OF THE PREFERRED EMBODIMENT

Referring more particularly to FIG. 1, a probe system, indicated as 10, comprises a tube 12 having an inlet end 14. An outer tube 16 is located concentrically about tube 12, the upper end of tube 16 being sealed with the peripheral surface of tube 12, as at 18, to define an annular chamber 20 having a lower open end 22.

A probe-driving arm 24, affixed to tube 12, and a drive mechanism 25 are provided for moving the probe arrangement 10 rectilinearly, as indicated by the arrows, to immerse and withdraw inlet end 14 from a liquid receptacle 26 located at a take-off station beneath tube 12. It should be understood that a number of receptacles 26 can be automatically and successively positioned at the take-off station, as shown and described in the above-identified U.S. Pat. No. 3,241,432; also, arm 24 can be adapted to impart a rotational movement to position inlet end 14 of tube 12 with respect to a plurality of liquid receptacles arranged in fixed relative position.

The outlet of tube 12 is connected along a conduit 28, having branch conduits 30, 32, 34, which are connected to pumps 36, 38, 40, respectively. Also, the interior of annular chamber 20 is connected along conduit 42 to pump 44. Pumps 36, 38, 40 and 44 each have a predetermined pump rate and are independently operated in particular sequence by programmer 46, along leads 48, 50, 52 and 54, respectively.

As shown in FIG. 1, probe arrangement 10 can be operated either as a dispenser, that is, in association with pumps 36, 38 and 40, or a sampler, in association with pump 40, to successively direct liquid samples of controlled volume to an analytical system 56. Analytical system 56 is shown connected to the output of pump 40 along conduit 58 and may be of the type described in the above-identified U.S. Pat. No. 3,241,432.

With respect to dispenser operation, the outlet of pump 38 is connected along conduit 60 to waste, and the respective inlets of pumps 36 and 44 are connected along conduits 62 and 64 to a source 66 of immiscible liquid. The liquid contained in source 66 is characterized as being immiscible with liquid 68, whether a sample or reagent liquid, and as capable of preferentially wetting, to the exclusion of liquid 68, the peripheral and internal surfaces 70 and 72, respectively, of tube 12 (see FIGS. 4, 5 and 6), and the internal surfaces of conduits comprising the metering apparatus. For example, if such surfaces are formed of Teflon, either silicone oil or fluorocarbon oil can be employed as the immiscible liquid. If such surfaces are formed of polypropylene, a hydrocarbon oil, e.g. squalene, can be employed.

Initially, tube 12 is withdrawn from receptacle 26 and pump 38 and 44 are operating. Operation of pump 44 fills chamber 20 with the immiscible liquid from source 66, excess liquid flowing from the lower end 22 of chamber 20 and downward as a thin film 74 along peripheral surface 70 of tube 12 (see FIG. 4). As a thin liquid film 74 reaches inlet 14, it tends to bead over the inlet end 14, so as to be aspirated upwardly along tube 12 and conduits 28 and 32 and passed to waste along conduit 60. As shown in FIG. 4, surface 70 of tube 12 is coated with a thin film 74 of the immiscible liquid, the run-off forming a bead which is aspirated along tube 12.

To initiate the aspiration cycle, drive mechanism 25 is operated by programmer 46, along lead 76, to displace arm 24 downwardly and immerse inlet end 14 into receptacle 26 positioned at the take-off station. While inlet end 14 is immersed, programmer 46 deactivates pump 44, while continuing to operate pump 38 for a predetermined time interval, such as to aspirate liquid 68 into tube 12 (see FIG. 5). As the immiscible liquid preferentially wets the surfaces of tube 12, to the exclusion of the liquid being aspirated, the aspirated liquid tends to form a discrete segment 68' which is subsequently encased within such liquid 66 and prevented from contacting the interior surface 72 (see FIG. 6). Also, during immersion, only a portion of thin film 74 on peripheral surface 70 of tube 12 is wiped. Accordingly, during the immersion and aspiration cycles, the surfaces 70 and 72 of tube 12 are not in contact with the liquid 68.

The specific gravity of the immiscible liquid may be greater or less than that of liquid 68, which is generally aqueous. The immiscible liquid, e.g. fluorocarbon oil, wiped from peripheral surface 70 initially tends to form a thin film 77 over the surface of liquid 68 (See FIG. 5). When the weight of thin film 77 is sufficient to overcome the surface tension of liquid 68, such film tends to break-up as globules 73, which settle to the bottom of receptacle 26. Also, if the specific gravity of the immiscible liquid is less than that of liquid 68, the thin film of immiscible liquid would remain over the surface of liquid 68 as film 77, but would not interfere with, impede or contaminate successive aspirations of liquid 68.

When pump 38 has been operated for a period to aspirate a liquid segment 68' of predetermined volume, programmer 46 deactivates such pump and controls drive mechanism 25 to withdraw tube 12 from receptacle 26. As tube 12 is being withdrawn, programmer 46 operates pump 44 to again flow immiscible liquid downwardly along peripheral surface 70 for aspiration along tube 12 by the action of pump 38. At such time, the aspirated liquid 68' of FIG. 5 would be encased within immiscible liquid 66, as shown in FIG. 6. As in FIG. 5, the spacing between the aspirated liquid segments and the surface 72 are exaggerated, for purposes of illustration.

Operating as a dispenser, a receiving receptacle 76 is substituted at the take-off station, as shown in FIG. 3. At such time, programmer 46 deactivates pumps 38 and 44 and operates pump 36 to force immiscible liquid along conduits 30 and 28 and outwardly through tube 12, forcing the liquid segment 68' into receptacle 76. Again, any immiscible liquid dispensed from tube 12 tends to sink within the dispensed liquid to form a thin layer 79 at the bottom of receptacle 76, such as not to interfere either with the addition of other liquids into receptacle 76 or with any reaction therebetween. When liquid segment 68' has been dispensed, programmer 46 deactivates pump 36 and operates pumps 38 and 44 to again flow immiscible liquid from source 68 along surface 70 for aspiration along tube 12. As both peripheral and interior surfaces 70 and 72 are uncontaminated, the probe arrangement 10 is immediately available for a next subsequent dispensing operation.

Also, the probe arrangement 10 can be adapted to aspirate and dispense multiple liquids in timed sequence without contamination therebetween. For example, assume that liquid 68 is a first reagent and that segment 68' has been aspirated along tube 12 and that tube 12 has been withdrawn from receptacle 26, as described. At such time, pumps 38 and 44 are operated and drive mechanism 25 displaces arm 24 to immerse tube 12 into a second receptacle 26', now positioned at the take-off station and containing a liquid 69. While tube 12 is withdrawn, a first aspirated liquid segment 68' (See FIG. 6) is displaced along tube 12 while immiscible liquid 66 is being aspirated along tube 12, as described. Upon immersion of tube 12 into liquid 69, programmer 46 controls pump 38 to aspirate a segment 69' of liquid 69 of predetermined volume along tube 12; concurrently, programmer 46 deactivates pump 44, pump 36 being inactive. As shown in FIG. 6, liquid segments 68' and 69' are maintained discrete from each other by immiscible liquid which has been aspirated therebetween and neither is in contact with the internal surface 72 of tube 12. It is evident that any number of liquids can be successively aspirated and maintained discrete along tube 12. Subsequently, pump 36 can be controlled by programmer 46, along lead 48 to dispense any number of successively aspirated liquid segments, e.g., 68' and 69', either in spaced-timed fashion, as desired, or in immediate sequence. However, dispensed, and referring to FIG. 3, the successively aspirated liquid segments can be intermixed, immiscible liquid settling as a thin layer 73 at the bottom receptacle 76, so as to be effectively removed.

Alternatively, when probe arrangement 10 is operated as a sampler, receptacles 68, 68', etc., each containing a sample to be analyzed can be advanced to the take-off station, in turn, by conventional apparatus. In such event, programmer 46 operates pump 40 continuously and operates pump 44 only during the withdrawal cycle, to allow for the aspiration of immiscible liquid segments between successively aspirated samples. As illustrated in FIG. 6, the successively aspirated sample liquids, e.g., 68' and 69', are passed by pump 40 along conduits 28, 34 and 58 to analyzer 56, which analyzer is more particularly described in the above-identified U.S. Pat. No. 3,479,141.

With respect to the aspiration of successive samples, as described, an air bubble can be included between successive samples, as also taught in the above-identified U.S. Pat. No. 3,479,141, by operating programmer 46 to momentarily deactivate pump 44 during the withdrawal cycle. Accordingly, the flow of immiscible liquid film 74 along surface 70 of tube 12 is interrupted for a time sufficient to aspirate an air segment along tube 12. In such event, adjacent segments 68, 68', etc., of liquid samples are separated by a sequence of immiscible liquid - air - immiscible liquid segments, each liquid sample segment and air bubble being fully encased within the immiscible liquid and not contacting the internal surface 72 of tube 12 or the internal surfaces of conduits 28, 34 or 58 to analyzer 56.

While the presently preferred forms of the metering apparatus have been described, it will be apparent, especially to those versed in the art, that the invention may take other forms and is susceptible of various changes in details without departing from the principles of the invention.

What is claimed is:
1. A liquid metering system comprising:
   a probe having an inlet end for immersion into a receptacle containing a first liquid to be aspirated,
   means for coating at least an outer peripheral surface of said probe with a second liquid, said second liquid being immiscible with said first liquid and which preferentially wets said surface of said probe to the substantial exclusion of said first liquid,
   means for immersing said probe into said first liquid, and
   means connected to an outlet end of said probe and operative while said probe is immersed in said first liquid for aspirating said first liquid.
2. A metering system as defined in claim 1, further including means for dispensing said aspirated first liquid along said probe.
3. A metering system as defined in claim 1, wherein the specific density of said second liquid is greater than that of said first liquid.
4. A metering system as defined in claim 1, wherein the specific density of said second liquid is less than that of said first liquid.
5. A metering system as defined in claim 1, wherein said second liquid is selected from the group consisting of fluorocarbon oil, hydrocarbon oil and silicone oil.
6. A metering system as defined in claim 1, wherein said coating means is operative to coat the internal surfaces of said probe with said second liquid.
7. A metering system as defined in claim 1, wherein said coating means includes means for flowing said second liquid along said outer peripheral surface of said probe.
8. A metering system as defined in claim 7, wherein said flowing means includes an annular chamber located concentrically about said probe, and means for pumping second liquid into said chamber, excess of said second liquid flowing along said outer peripheral surface to said inlet end of said probe.
9. A metering system as defined in claim 8, wherein said annular chamber is formed integrally with said probe.
10. A metering system as defined in claim 7, wherein said coating means includes means for flowing said second liquid along said outer peripheral surface to said inlet end of said probe.
11. A metering system as defined in claim 10, wherein said flowing means and said aspirating means being operative while said probe is withdrawn from said first liquid, such that at least a portion of said second liquid flowed along said outer peripheral surface is aspirated along said inlet end of said probe.
12. A metering system, as defined in claim 11, wherein said flowing means and said aspirating means have substantially the same flow capacity.
13. A metering system as defined in claim 1, further including means for immersing said probe into two or more successive receptacles containing different first liquids, said flowing means and said aspirating means being operative while said probe is withdrawn from said receptacles, such that a segment of said second liquid is aspirated along said probe between successive segments of said different first liquids.
14. A metering system as defined in claim 13, further including means for selectively dispensing segments of said different first liquids aspirated along said probe in controlled time sequence.

15. A metering system as defined in claim 13, further including means for substantially concurrently dispensing said segments of said different first liquids aspirated along said probe.

16. A metering system as defined in claim 13, further including analytical means connected to the outlet of said probe for analyzing said first liquid segments, in turn, and means for passing said first liquid segments to said analytical means.

17. A metering system as defined in claim 13, further including means for deactivating said flowing means while said probe is withdrawn, such that a segment of air is aspirated along said probe between said successive segments of said different first liquids.

18. A metering system as defined in claim 1, further including first and second conduits connected to said outlet end of said probe, first and second pumping means connected to said first and second conduits, respectively, said first pumping means being operative to aspirate along said probe and said second pumping means being operative to dispense along said probe, and programming means for controlling the operation of said first and second pumping means.

19. A metering system as defined in claim 18, said programming means is connected to said immersing means, said programming means being operative to control the relative operations of said immersing means and said first and second pumping means.

* * * * *